United States Patent
Arakawa et al.

(10) Patent No.: US 8,253,939 B2
(45) Date of Patent: Aug. 28, 2012

(54) PARTICLE COUNTER

(75) Inventors: Akira Arakawa, Kyoto (JP); Takahiro Mori, Kyoto (JP); Tsunehiro Inoue, Omihachiman (JP)

(73) Assignee: Shimadzu Corporation, Kyoto (JP)

( * ) Notice: Subject to any disclaimer, the term of this patent is extended or adjusted under 35 U.S.C. 154(b) by 453 days.

(21) Appl. No.: 12/627,551

(22) Filed: Nov. 30, 2009

(65) Prior Publication Data
US 2010/0134797 A1 Jun. 3, 2010

(30) Foreign Application Priority Data
Nov. 28, 2008 (JP) .................................. 2008-305370

(51) Int. Cl.
*G01N 21/00* (2006.01)
(52) U.S. Cl. .......................... 356/338; 356/432; 356/437
(58) Field of Classification Search ........... 356/335–344
See application file for complete search history.

(56) References Cited

U.S. PATENT DOCUMENTS

| | | | |
|---|---|---|---|
| 4,330,731 A * | 5/1982 | Garin et al. | 313/104 |
| 4,870,942 A * | 10/1989 | Shibata et al. | 123/676 |
| 4,928,537 A * | 5/1990 | Liu et al. | 73/863.86 |
| 5,027,642 A * | 7/1991 | Wen et al. | 73/23.2 |
| 5,192,870 A * | 3/1993 | Batchelder et al. | 250/574 |
| 5,247,188 A * | 9/1993 | Borden | 250/574 |
| 6,737,666 B1 * | 5/2004 | Ito et al. | 250/574 |
| 7,323,881 B2 * | 1/2008 | Lopez Alvarez | 324/536 |

FOREIGN PATENT DOCUMENTS
JP 06-026823 A 2/1994
* cited by examiner

*Primary Examiner* — Gregory J Toatley
*Assistant Examiner* — Jarreas C Underwood
(74) *Attorney, Agent, or Firm* — Sughrue Mion, PLLC

(57) ABSTRACT

The present invention provides a particle counter capable of sensitively determining the contamination level of a light transmission window. The particle counter according to the present invention includes: a light source 281 for emitting light through a light incident window 24 to a measurement area 40 in a vacuum state or in an approximately vacuum state; a scattered light detector 32 for detecting scattered light through a detection window 30, the scattered light being generated when a light is delivered to the measurement area 40; a vacuum gauge 12 for measuring the pressure of the measurement area 40; a signal processor 13 for converting a detection signal of the scattered light into an electrical signal; and a contamination level determiner 19 for determining the contamination level of the transmission window from the time average of the electrical signal and the pressure.

5 Claims, 3 Drawing Sheets

PARTICLE COUNTER

The present invention relates to a particle counter for counting the number of particles such as solid particles contained in the emission gas of semiconductor manufacturing equipment and other apparatuses.

BACKGROUND OF THE INVENTION

Dust particles generated during the process of producing semiconductors degrades the products. Therefore, semiconductor manufacturing equipments are normally equipped with a particle counter for counting in real time the number of particles generated in the process chamber (refer to Patent Document 1).

The particle counter is generally provided in an exhaust pipe from the process chamber and includes: a light source for emitting a laser light to a measurement area in the exhaust pipe; a detector for detecting the light scattered by a particle irradiated with the laser light; a discriminator for determining whether or not a particle exists by comparing the detection signal of the detector with a predetermined specific discrimination threshold; and other units.

The exhaust pipe is provided with a light incident window, through which laser light from the light source is delivered to the measurement area. The scattered light generated by a particle irradiated with the laser light enters the detector through the light detection window. While most of the particles flowing in the exhaust pipe pass through the measurement area with the emitted gas, some particles are adhered to the light incident window and light detection window (hereinafter, both of which will be simply called "windows") by electrostatic force and other factors. When particles are thus adhered to the windows, the stray light, which is generated by the laser light scattered by other places in the exhaust pipe, is scattered by the particles adhered to the windows and, as well as the laser light scattered by the particles passing through the measurement area, enters the detector.

The stray light scattered by the particles adhered to the windows becomes a factor of high frequency component of the scattered light signal detected and generated by the detector. Hence, in conventional particle counters, the contamination level of the windows is determined based on the magnitude of the high frequency component of the scattered light detection signal.*

Patent Document 1: Japanese Unexamined Patent Application Publication No. H06-26823

SUMMARY OF THE INVENTION

The high frequency component of the electrical signal of the scattered light is affected by a plurality of factors such as the degree of vacuum of the measurement area and the electrical noise from peripheral devises. Therefore, the contamination level of the light incident window and light detection window cannot be accurately determined only from the high frequency component of the electrical signal.

The problem to be solved by the present invention is to provide a particle counter capable of sensitively determining the contamination level of the light incident window and light detection window.

The present invention achieved to solve the aforementioned problem provides a particle counter including:

a) a light emitter for emitting a light to a measurement area in a vacuum state or in a near vacuum state, the light being thrown through a light incident window;

b) a scattered light detector for detecting a scattered light coming out through a light detection window and for generating an electrical signal corresponding to the scattered light, the scattered light being generated when a light is thrown to the measurement area;

c) a vacuum measurement means for measuring the degree of vacuum of the measurement area; and d) a determiner for making a determination relating to the contamination level of the light incident window and/or the light detection window from a time average of the electrical signal and the degree of vacuum.

The light incident window and the light detection window may be the same window. That is, the scattered light may enter the detector through the window through which the light is thrown to the measurement area. Furthermore, a window other than the light incident window and the light detection window may be provided in the measurement area.

It is preferable that, for the aforementioned "time average of the electrical signal", the time average of the electrical signal of light scattered by particles flowing through the measurement area over the time twice or more of the peak width is taken.

The scattered light detector detects the light scattered by the particles flowing through the measurement area, and also detects the light produced by the stray light scattered by the particles adhered to the light transmission window, i.e. the light detection window. The time average of the electrical signal of the scattered light detection signal has high-frequency components removed and hence does not include the electrical signal of the light scattered by the particles flowing through the measurement area. The time average of the electrical signal of the scattered light detection signal varies depending on the degree of vacuum of the measurement area. Therefore, it is possible to determine the intensity of the stray light produced by particles adhered to the light transmission window, i.e. the contamination level of the light transmission window, based on the degree of vacuum of the measurement area and the time average of the electrical signal of the scattered light detection signal.

EXPLANATION OF THE NUMERALS

10 . . . Detector
12 . . . Vacuum Gauge

13 . . . Signal processor
16 . . . Threshold Setting Unit
18 . . . Threshold Discriminator
19 . . . Contamination Level Determiner
20 . . . Counter
22 . . . Exhaust Pipe
24 . . . Light Incident Window
26 . . . Light Exit Window
28 . . . Light Irradiator
281 . . . Light Source
30 . . . Detection Window
32 . . . Scattered Light Detector
34 . . . Condenser Lens
40 . . . Measurement Area

DETAILED DESCRIPTION OF PREFERRED EMBODIMENTS

Hereinafter, an embodiment of the present invention is described in detail with reference to the attached drawings.

Figure 1:
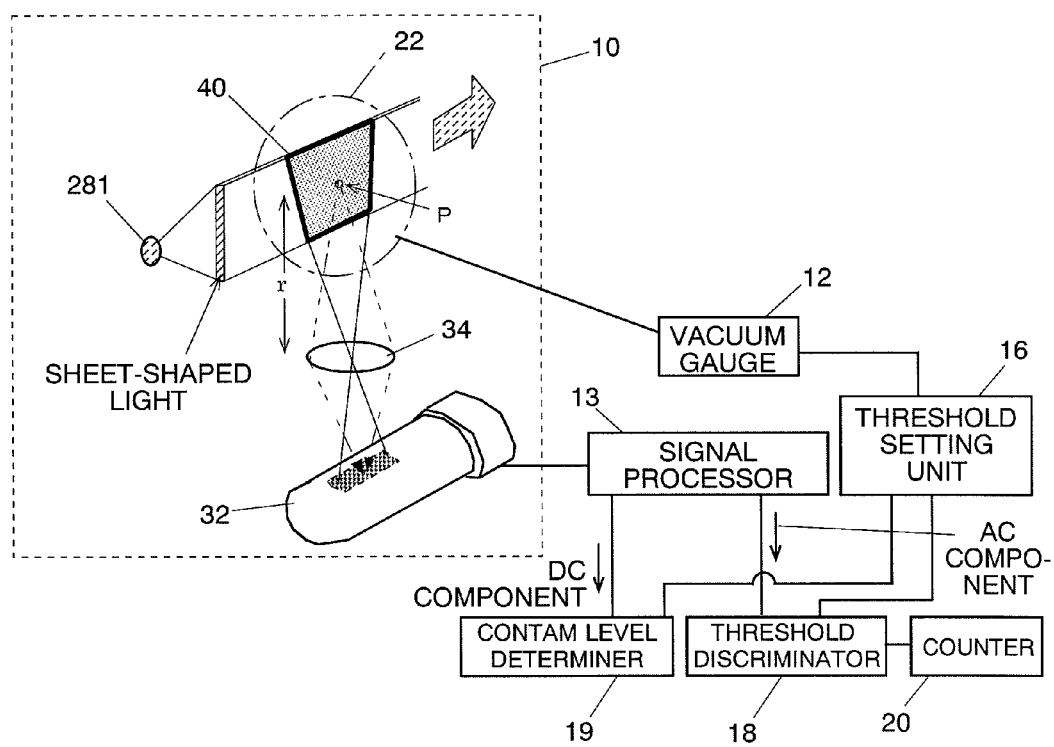
FIG. 1 is a schematic configuration diagram of an entire particle counter according to the first embodiment of the present invention.

FIG. 1 is a schematic configuration diagram of the particle counter according to the present embodiment. The particle counter 1 is composed of a detector 10, a vacuum gauge 12, a signal processor 13, a threshold setting unit 16, a threshold discriminator 18, a contamination level determiner 19, a counter 20, and other units.

Figure 2:
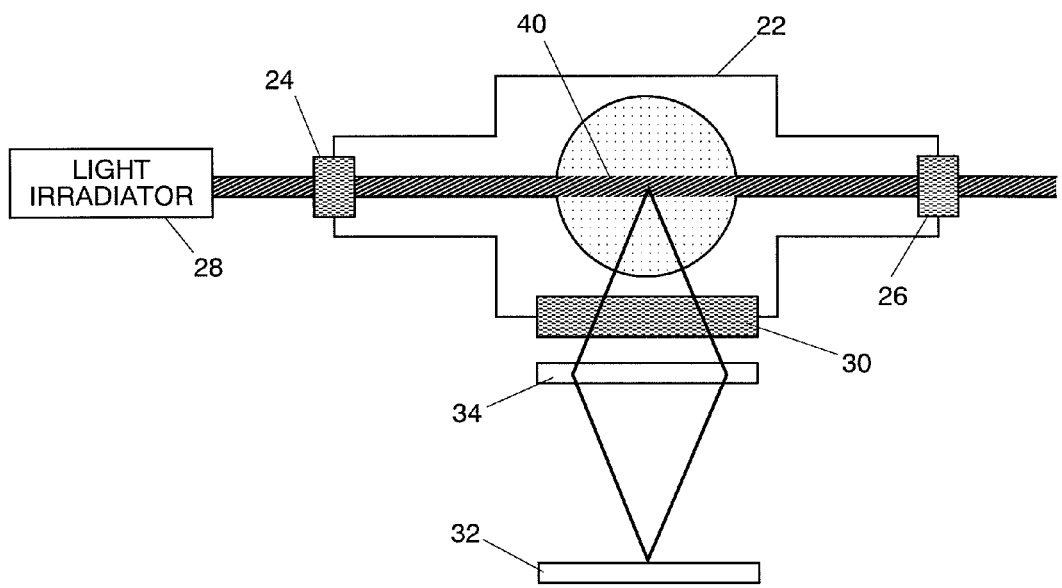
FIG. 2 is a schematic diagram of a light detector provided in an exhaust pipe.

As illustrated in FIGS. 1 and 2, the detector 10 is provided in the exhaust pipe 22 of semiconductor manufacturing equipment for example. The inside of the exhaust pipe 22 is in a vacuum state or in a near vacuum state, and a particle P flows in the direction perpendicular to the paper plane (e.g. from the front to the back of the paper plane) of FIG. 2.

The detector 10 has: a light incident window 24 and a light exit window 26 which are placed on the opposite walls of the exhaust pipe 22; a light irradiator 28 for delivering a laser light toward the light exit window 26 through the light incident window 24; a detection window 30 provided on a wall of the exhaust pipe 22 lying normal to the direction substantially perpendicular to the direction of the irradiation of the laser light; a scattered light detector 32 for detecting the scattered light that has passed through the detection window 30; a condenser lens 34 placed between the detection window 30 and the scattered light detector 32; and other components.

The light irradiator 28 is composed of: a light source 281 which is a semiconductor laser element or other illuminant; and a lens (not shown) for converting the laser light of the light source 281 into sheet-shaped light. The sheet-shaped light emitted from the light irradiator 28 enters the exhaust pipe 22 through the light incident window 24, passes through the inside of the exhaust pipe 22 (which is in vacuum), and then exits from the light exit window 26. Accordingly, the light is thrown to a rectangular sheet-like measurement area 40 in the exhaust pipe 22, and particles flowing through the measurement area 40 generate scattered light. A portion of the scattered light generated in the measurement area 40 passes through the detection window 30 and is converged to the scattered light detector 32 by the condenser lens 34.

The scattered light detected by the scattered light detector 32 is converted to an electrical signal, which is provided to a signal processor 13. The signal processor 13 divides the electrical signal into the direct-current (DC) component and alternate-current (AC) component, and provides them to the contamination level determiner 19 and the threshold discriminator 18, respectively. The DC component is obtained by integrating the electrical signal of the scattered light with a time constant sufficiently longer than the duration of the pulse signal of the scattered light, and represents the time average of the electrical signal. In the present embodiment, the DC component is the time average over 100 msec, for example. The AC component is obtained by subtracting the DC component from the electrical signal of the scattered light.

The threshold discriminator 18 compares the AC component provided from the signal processor 13 with a discrimination threshold. When the AC component exceeds the threshold, the threshold discriminator 18 determines that a particle has passed, and provides a determination signal to the counter 20. The counter 20 counts the number of determination signals within a predetermined time, i.e. the number of particles that have passed through the measurement area within the predetermined time.

Figure 3:
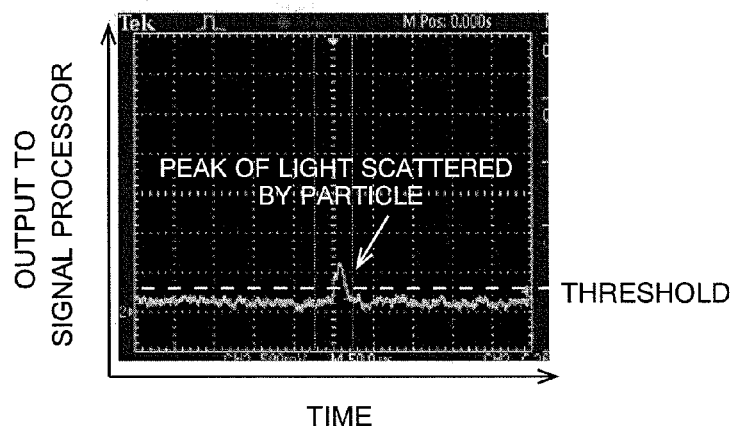
FIG. 3 is a diagram illustrating the relationship among a discrimination threshold, an AC component, and a peak of light scattered by a particle.

FIG. 3 illustrates the relationship among the threshold value, the AC component, and a peak of scattered light due to a particle. The AC component, which is normally below the threshold, will exceed the threshold when a peak due to the light scattered by a particle appears (as indicated by the arrow in FIG. 3).

The contamination level determiner 19 compares the DC component provided from the signal processor 13 with contamination level determination values provided from the threshold setting unit 16 to determine the contamination level.

The number of particles counted by the counter 20 and the result of determination by the contamination level determiner 19 are shown on the display (which is not illustrated). Accordingly, by looking at the display, a user can find out the number of particles and whether or not the light incident window 24 and other portions are contaminated.

The degree of vacuum (or pressure) of the inside of the exhaust pipe 22 is measured by the vacuum gauge 12, and the threshold setting unit 16 sets the discrimination value and contamination level determination values based on the degree of vacuum. The threshold setting unit 16 may change the discrimination value and/or the contamination level determination values according to a change in the degree of vacuum, or may set the discrimination value and/or the contamination level determination values based on the average value of the degree of vacuum over a predetermined time.

The detection signal of the scattered light detector 32 is now described. The light entering the scattered light detector 32 includes not only the light scattered by particles but also a stray light scattered by the particles adhered to the light incident window 24, light exit window 26 and detection window 30 and background light by the molecules of gas such as oxygen, nitrogen and other elements existing in the measurement area 40. Some particles flowing in the exhaust pipe 22 adhere to the light incident window 24, light exit window 26, and detection window 30 by the electrostatic force or other factors. The particles adhered to the light incident window 24 and other portions generate scattered light when light is thrown. Gas of oxygen, nitrogen, and other elements is also composed of a group of very small particles, and therefore scatters light when light is thrown to them, as in the case of the dust particles.

Accordingly, the detection signal of the scattered light detector 32 includes the stray light and the background light scattered by the particles adhered to the light incident window 24, to which the light scattered by the particles flowing through the measurement area 40 is added.

For example, when a non-polarized plane wave (having an intensity of $I_0$) is thrown to an isolated particle in vacuum, where the particle has the radius of a which is sufficiently smaller than the wavelength of light, the ratio [intensity of scattered light Iscat/intensity of thrown light $I_0$] at the distance r from the particle can be obtained by the following equation (1) based on the Rayleigh theory:

$$\frac{I_{scat}}{I_{0\_unpol}} = \frac{I_1 + I_2}{2} = \frac{8\pi^4 a^6}{r^2 \lambda^4}\left(\frac{n^2-1}{n^2+2}\right)(1+\cos^2\theta) \quad (1)$$

where α is the radius of the particle, r is the distance from the scattered particle, λ is the wavelength of light, n is the refractive index of the particle, and θ is the angle between the incident light and scattered light.

The intensity of light scattered by the molecules of gas such as oxygen and nitrogen is proportional to the value calculated by the intensity of light scattered by one gas molecule (which is calculated by equation (1)) multiplied by the number of gas molecules. Since the number of gas molecules existing in the measurement area 40 is proportional to the pressure, the intensity of background light due to the gas molecules is proportional to the pressure.

For example, the intensity of light scattered by a large number of nitrogen molecules and the intensity of light scattered by a particle are compared, where the diameter of a nitrogen gas molecule is supposed to be 0.2 nm and that of the particle is 200 nm. Equation (1) shows that the intensity of scattered light is proportional to the sixth power of the diameter of a particle. Under the aforementioned suppositions, the diameter of the particle is 1000 ($=10^3$) times larger than the nitrogen molecules, so that the intensity due to the particle is $10^{18}$ times stronger than that due to the nitrogen molecules. Supposing, for example, that the degree of vacuum is 1 atm and the volume of the detection area is 0.2 ml, the number of molecules existing in the area is 5.357×1018 ($=6\times10^{23}/22.4\times 0.2\times10^{-3}$). This indicates that the light scattered by the molecules of nitrogen at 1 atm is greater than the light scattered by a particle of 200 nm.

The intensity of the background light due to the gas molecules existing in the measurement area 40 is uniquely determined when the degree of vacuum of the measurement area 40 is known. Therefore, based on the degree of vacuum, the threshold setting unit 16 sets the discrimination threshold value so that the background light (or voltage signal) is not counted as a light scattered by a particle.

Figure 4:
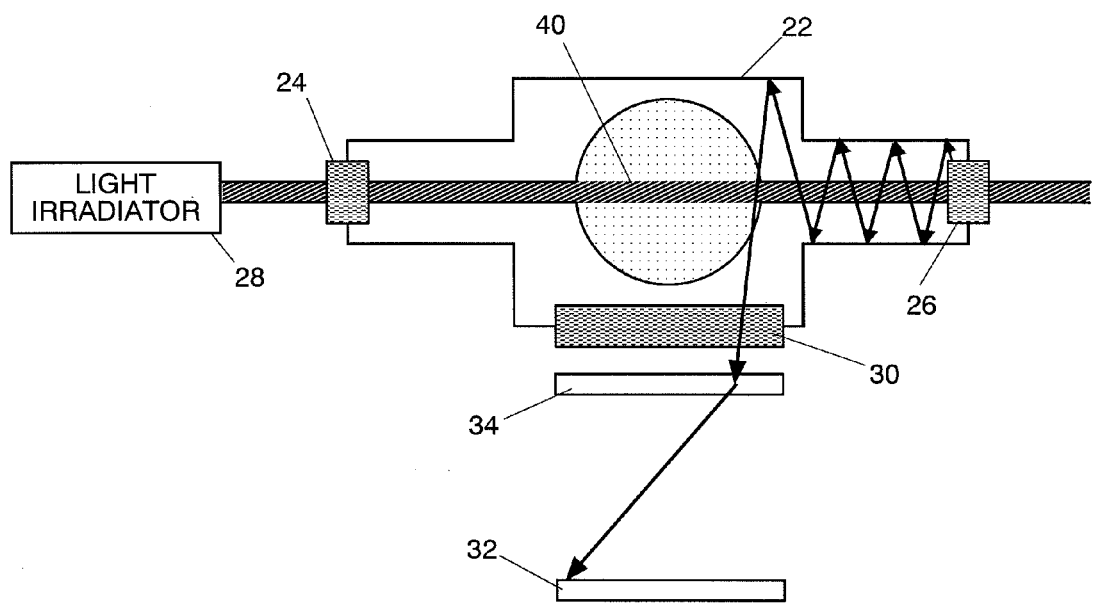
FIG. 4 is a diagram for explaining a stray light produced by particles adhered to the light exit window.

The light scattered by the particles adhered to the light incident window 24 and other portions is reflected a plurality of times in the exhaust pipe 22 and then passes through the detection window 30 to enter the scattered light detector 32 (refer to FIG. 4). The time-averaging operation of the electrical signal obtained by converting the detection signal (or intensity) of the scattered light removes high-frequency components from the signal and leaves only the DC component which does not contain the electrical signal of the light scattered by the particles flowing through the measurement area. Hence, the time average of the electrical signal equals the sum of the background light and the stray light due to the particles adhered to the light incident window and other portions. The DC component varies according to the degree of vacuum, or pressure. In addition, as stated earlier, the intensity of the background light due to gas molecules existing in the measurement area 40 is uniquely determined when the pressure of the measurement area 40 is known. Accordingly, the contamination level of the window can be determined from the pressure and the DC component.

Figure 5:
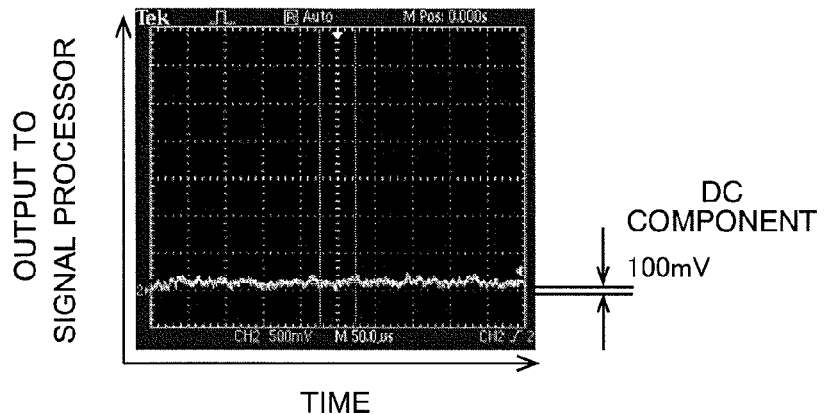
FIG. 5 is a diagram illustrating the waveform of the electrical signal of the scattered light generated near the entrance of the measurement area when the light incident window and other units are not contaminated.
Figure 6:
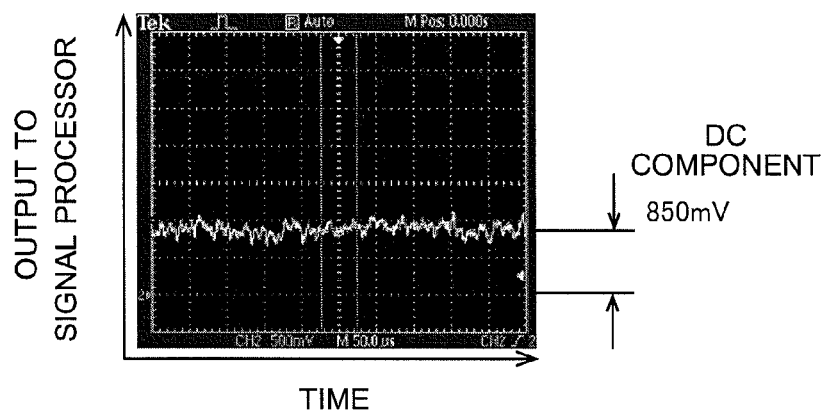
FIG. 6 is a diagram illustrating the waveform of the electrical signal of the scattered light generated near the entrance of the measurement area when the light incident window and other units are moderately contaminated.
Figure 7:
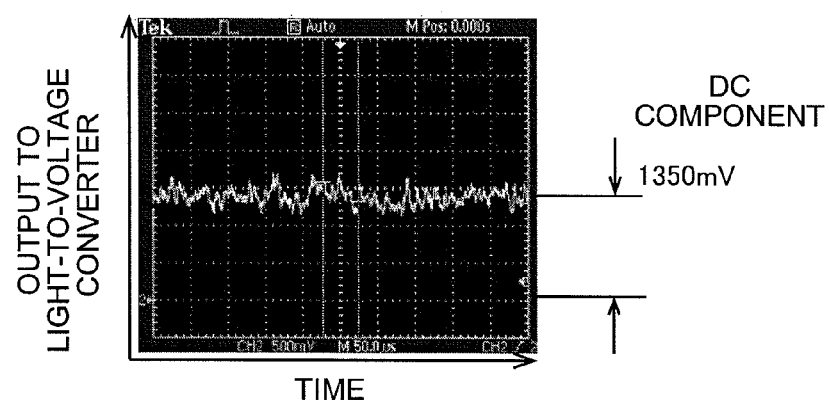
FIG. 7 is a diagram illustrating the waveform of the electrical signal of the scattered light generated near the entrance of the measurement area when the light incident window and other units are much contaminated.

FIGS. 5 through 7 each illustrate an example of the waveform of the electrical signal of the signal processor 13. In every example, the pressure measured by the vacuum gauge 21 is 40 Torr, and no particles are flowing through the measurement area 40.

FIG. 5 illustrates the waveform of the electrical signal recorded when none of the windows was contaminated. In this case, a DC component of 100 mV was observed in the electrical signal.

FIG. 6 illustrates the waveform of the electrical signal recorded when the windows were moderately contaminated. In this case, a DC component of 850 mV was observed.

FIG. 7 illustrates the waveform of the electrical signal recorded when the windows were much contaminated. In this case, a DC component of 1350 mV was observed.

As is evident from FIGS. 5 through 7, even with the same pressure, the DC component increases as the contamination level of the windows increases. Therefore, the contamination level of the windows can be determined from the discrimination threshold, which is set based on the pressure, and the time average (or DC component) of the electrical signal.

For example, suppose that the particle counter operates within a range from 10 Torr to the atmospheric pressure (760 Torr). In addition, suppose that the DC component due to the background light of the gas is 10 mV when the pressure is 10 Ton and the windows are clean. Since the DC component is proportional to the pressure, the DC component by the background light of gas will be 760 mV at the atmospheric pressure (760 Torr). Therefore, if the pressure is known, it is possible to set the contamination level determination value at a level slightly higher than the DC component due to the background light of the gas. That is, if the pressure is found to be 10 Ton, the contamination level determination value can be set to 20 mV. Similarly, if the pressure is found to be 760 Torr, the contamination level determination value can be set to be 770 mV.

In the case where the pressure is not measured, it is not possible to determine whether or not an increase in the DC component is due to a change in the pressure. Hence, the determination threshold of the contamination level of the windows should always be set to be slightly greater than 760 mV, i.e. the electrical signal of the background light of the gas at the atmospheric pressure (e.g. 800 mV).

Thus, by combining the pressure and the DC component, the detection sensitivity to the contamination level of the windows can be improved to a level 800/20=40 times higher than achieved without measuring the pressure.

What is claimed is:
1. A particle counter comprising:
   a) a light emitter for emitting a light to a measurement area in a vacuum state or in a near vacuum state, the light being thrown through a light incident window;
   b) a scattered light detector for detecting a scattered light coming out through a light detection window and for generating an electrical signal corresponding to the scattered light, the scattered light being generated when a light is thrown to the measurement area;
   c) a vacuum measurement means for measuring a degree of vacuum of the measurement area; and
   d) a determiner for making a determination relating to a contamination level of the light incident window and/or the light detection window from a time average of the electrical signal and the degree of vacuum.
2. The particle counter according to claim 1, wherein the light incident window and the light detection window are the same.

3. The particle counter according to claim 1, wherein the determiner takes the time average of the electrical signal over a time twice or more of a peak width.

4. The particle counter according to claim 2, wherein the determiner takes the time average of the electrical signal over a time twice or more of a peak width.

5. The particle counter according to claim 1, wherein the vacuum measurement means measures a pressure of the measurement area.

* * * * *